US00PP19736P2

(12) United States Plant Patent
Bergman

(10) Patent No.: US PP19,736 P2
(45) Date of Patent: Feb. 17, 2009

(54) ***CHRYSANTHEMUM* PLANT NAMED 'YODURANGO'**

(50) Latin Name: *Chrysanthemum×morifolium*
Varietal Denomination: Yodurango

(75) Inventor: Wendy R. Bergman, Lehigh Acres, FL (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 11/983,742

(22) Filed: Nov. 12, 2007

(51) Int. Cl.
*A01H 5/00* (2006.01)

(52) U.S. Cl. ..... Plt./290

(58) Field of Classification Search ..... Plt./290
See application file for complete search history.

*Primary Examiner*—Annette H Para
*Assistant Examiner*—June Hwu
(74) *Attorney, Agent, or Firm*—C. A. Whealy

(57) ABSTRACT

A new and distinct cultivar of *Chrysanthemum* plant named 'Yodurango', characterized by its compact, upright and uniformly mounded plant habit; freely branching habit; dark green-colored foliage; uniform flowering response; early flowering habit; decorative-type inflorescences with orange bronze-colored ray florets; and excellent postproduction longevity with plants maintaining good substance and color for about four weeks in an interior environment.

2 Drawing Sheets

Botanical designation: *Chrysanthemum×morifolium.*
Cultivar denomination: 'Yodurango'.

BACKGROUND OF THE INVENTION

The present invention relates to a new and distinct cultivar of *Chrysanthemum* plant, botanically known as *Chrysanthemum×morifolium,* commercially grown as a pot-type *Chrysanthemum* and hereinafter referred to by the name 'Yodurango'.

The objective of the breeding program is to create new pot-type *Chrysanthemum* cultivars that are suitable for year-round production with uniform plant growth habit, freely branching habit, good vigor, desirable inflorescence form and floret colors, fast response time and excellent postproduction longevity.

The new *Chrysanthemum* originated from a cross-pollination made by the Inventor in March, 2003, in Salinas, Calif. of a proprietary selection of *Chrysanthemum× morifolium* identified as code number YB-A4033, not patented, as the female, or seed, parent with a proprietary selection of *Chrysanthemum×morifolium* identified as code number YB-A4512, not patented, as the male, or pollen, parent. The new *Chrysanthemum* was discovered and selected by the Inventor as a single flowering plant within the progeny of the stated cross-pollination in a controlled environment in Fort Myers, Fla. in February, 2004. The selection of this plant was based on its uniform plant growth habit, freely branching habit, good vigor, desirable inflorescence form and floret coloration, fast response time and excellent postproduction longevity.

Asexual reproduction of the new *Chrysanthemum* by vegetative tip cuttings was first conducted in Fort Myers, Fla. in May, 2004. Asexual reproduction by cuttings has shown that the unique features of this new *Chrysanthemum* are stable and reproduced true to type in successive generations.

SUMMARY OF THE INVENTION

Plants of the cultivar Yodurango have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yodurango'. These characteristics in combination distinguish 'Yodurango' as a new and distinct potted *Chrysanthemum* cultivar:

1. Compact, upright and uniformly mounded plant habit.
2. Freely branching habit.
3. Dark green-colored foliage.
4. Uniform flowering response.
5. Can be grown disbudded, center-budded or as natural spray type.
6. Early flowering habit, 7.5-week response time.
7. Decorative-type inflorescences with orange bronze-colored ray florets.
8. Excellent postproduction longevity with plants maintaining good substance and color for about four weeks in an interior environment.

Plants of the new *Chrysanthemum* differ from plants of the female parent selection in the following characteristics:

1. Plants of the new *Chrysanthemum* are more compact than plants of the female parent selection.
2. Plants of the new *Chrysanthemum* flower earlier than plants of the female parent selection.
3. Plants of the new *Chrysanthemum* have lighter orange bronze-colored ray florets than plants of the female parent selection.

Plants of the new *Chrysanthemum* differ from plants of the male parent selection primarily in inflorescence form as inflorescences of plants of the new *Chrysanthemum* do not develop disc florets whereas inflorescences of plants of the male parent selection develop disc florets.

Plants of the new *Chrysanthemum* can be compared to plants of the *Chrysanthemum* cultivar Amber Pomona, disclosed in U.S. Plant Pat. No. 12,248. In side-by-side comparisons conducted in Fort Myers, Fla., plants of the new *Chrysanthemum* differed from plants of the cultivar Amber Pomona in the following characteristics:

1. Plants of the new *Chrysanthemum* were more compact than plants of the cultivar Amber Pomona.
2. Plants of the new *Chrysanthemum* flowered 1.5 weeks earlier than plants of the cultivar Amber Pomona.

BRIEF DESCRIPTION OF THE PHOTOGRAPHS

The accompanying photographs illustrate the overall appearance of the new *Chrysanthemum.* These photographs show the colors as true as it is reasonably possible to obtain in colored reproductions of this type. Colors in the photographs may differ slightly from the color values cited in the detailed botanical description which accurately describe the colors of the new *Chrysanthemum.*

The photograph on the first sheet comprises a side perspective view of typical flowering plants of 'Yodurango' grown in a container.

The photograph on the second sheet is a close-up view of typical inflorescences of 'Yodurango'.

DETAILED BOTANICAL DESCRIPTION

The aforementioned photographs and following observations and measurements describe plants grown in Leamington, Ontario, Canada during the spring in a glass-covered greenhouse and under conditions and practices which approximate those generally used in commercial pot-type *Chrysanthemum* production. During the production of the plants, day temperatures ranged from 21° C. to 27° C., night temperatures ranged from 17° C. to 19° C. and light levels ranged from 4,000 to 6,000 foot candles. Four unrooted cuttings were directly stuck in 15-cm containers, exposed to long day/short night conditions, and pinched about two weeks later. One week after the pinch, the photoinductive short day/long night treatments were started. Plants used in the photographs and for the description were disbudded and were about two months old. In the following description, color references are made to The Royal Horticultural Society Colour Chart, 1995 Edition, except where general terms of ordinary dictionary significance are used.

Botanical classification: *Chrysanthemum×morifolium* cultivar Yodurango.

Parentage:

*Female, or seed, parent.*—Proprietary selection of *Chrysanthemum×morifolium* identified as code number YB-A4033, not patented.

*Male, or pollen, parent.*—Proprietary selection of *Chrysanthemum×morifolium* identified as code number YB-A4512, not patented.

Propagation:

*Type.*—Terminal vegetative cuttings.

*Time to initiate roots.*—About four days at temperatures of about 21° C.

*Time to produce a rooted young plant.*—About ten days at temperatures of about 21° C.

*Root description.*—Medium thickness, fibrous; white in color.

*Rooting habit.*—Freely branching; moderately dense.

Plant description:

*Appearance.*—Herbaceous decorative pot-type *Chrysanthemum* typically grown as a disbudded, center-budded or as a natural spray type. Stems upright and outwardly spreading giving a uniformly mounded appearance to the plant. Freely branching habit, about four lateral branches develop after removal of terminal apex (pinching); dense and full plant habit. Strong and moderately vigorous growth habit.

*Plant height.*—About 27 cm.

*Plant width.*—About 36 cm.

*Lateral branches.*—Length: About 22 cm. Diameter: About 6 mm. Internode length: About 2 cm. Strength: Strong. Texture: Pubescent. Color: Darker than 144A to close to 146A.

Foliage description:

*Arrangement.*—Alternate, simple.

*Length.*—About 9.2 cm.

*Width.*—About 7.1 cm.

*Apex.*—Cuspidate to mucronate.

*Base.*—Attenuate with truncate tendencies.

*Margin.*—Palmately lobed, sinuses between lateral lobes parallel to convergent.

*Texture, upper and lower surfaces.*—Fine pubescence; veins prominent on lower surface.

*Color.*—Developing and fully expanded foliage, upper surface: Darker and more green than 147A; venation, close to 147A. Developing and fully expanded foliage, lower surface: Darker than 147B; venation, close to 147B.

*Petiole length.*—About 3.5 cm.

*Petiole diameter.*—About 4 mm.

*Petiole color, upper surface.*—147A.

*Petiole color, lower surface.*—147B.

Inflorescence description:

*Appearance.*—Decorative-type inflorescence form with elongated oblong-shaped ray florets. Inflorescences borne on terminals above foliage. Ray florets arranged acropetally on a capitulum. Inflorescence not fragrant. Typically grown as a center-budded type.

*Flowering response.*—Under natural conditions, plants flower in the autumn/winter in the Northern Hemisphere. At other times of the year, inflorescence initiation and development can be induced under short day/long night conditions (at least 13.5 hours of darkness). Early flowering habit; plants exposed to three weeks of long day/short night conditions followed by photoinductive short day/long night conditions flower about 7.5 weeks later.

*Postproduction longevity.*—Inflorescences maintain good color and substance for about four weeks in an interior environment.

*Quantity of inflorescences.*—Grown as a disbud, only one inflorescence develops per lateral stem or four inflorescences per plant.

*Inflorescence bud.*—Height: About 7 mm. Diameter: About 9 mm. Shape: Oblate. Color: Close to 146A.

*Inflorescence size.*—Diameter: About 9.25 cm. Depth (height): About 4 cm. Receptacle diameter: About 1 cm.

*Ray florets.*—Shape: Elongated-oblong. Orientation: Initially upright, then about 90° from vertical or perpendicular to peduncle to eventually reflexed. Aspect: Initially incurved, then mostly flat. Length:

About 4.6 cm. Width: About 1.1 cm. Corolla tube length: About 4 mm. Apex: Acute, emarginate or cuspidate. Base: Attenuate. Margin: Entire. Texture, upper and lower surfaces: Smooth, glabrous, satiny. Number of ray florets per inflorescence: About 202 arranged in numerous rows. Color: When opening, upper and lower surfaces: Close to 144A becoming closer to 154A with development. Fully opened, upper surface: 6A overlain with close to 163A; color becoming closer to 6A with development. Fully opened, lower surface: 6C to 6D underlain with close to 163A; color becoming closer to 6D with development.

*Disc florets.*—No disc florets observed.

*Phyllaries.*—Number of phyllaries per inflorescence: About 26. Length: About 1.1 cm. Width: About 3 mm. Shape: Lanceolate. Apex: Acute. Base: Truncate. Texture, upper surface: Smooth, waxy. Texture, lower surface: Pubescent. Color, upper and lower surfaces: Close to 146A.

*Reproductive organs.*—Androecium: None observed. Gynoecium: Pistil length: About 1 cm. Stigma shape: Bi-parted. Stigma color: Close to 9A. Style length: About 7 mm. Style color: Close to 145D. Ovary color: Close to 157A.

*Seed/fruit.*—Seed and fruit production has not been observed.

Disease/pest resistance: Resistance to pathogens and pests common to *Chrysanthemums* has not been observed on plants grown under commercial conditions.

Temperature tolerance: Plants of the new *Chrysanthemum* have been observed to tolerate temperatures ranging from about 1° C. to about 38° C.

It is claimed:

1. A new and distinct *Chrysanthemum* plant named 'Yodurango' as illustrated and described.

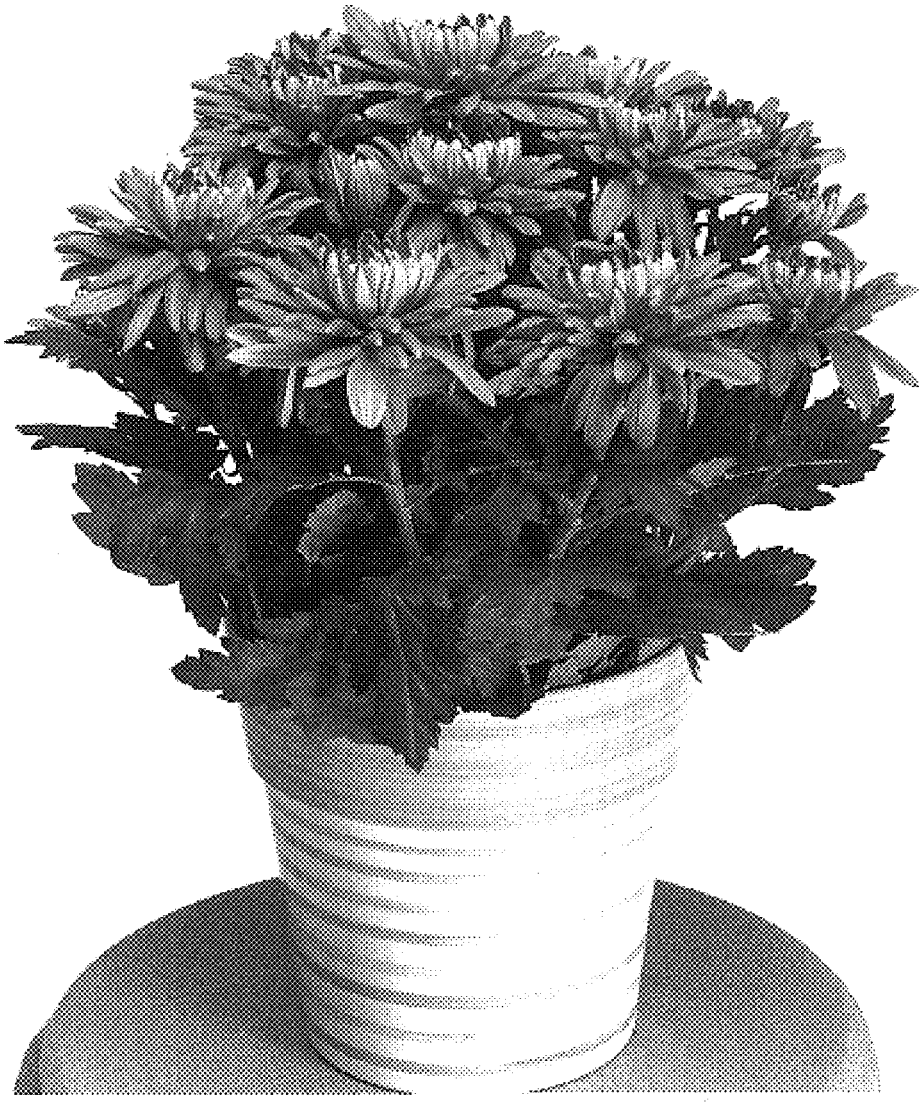

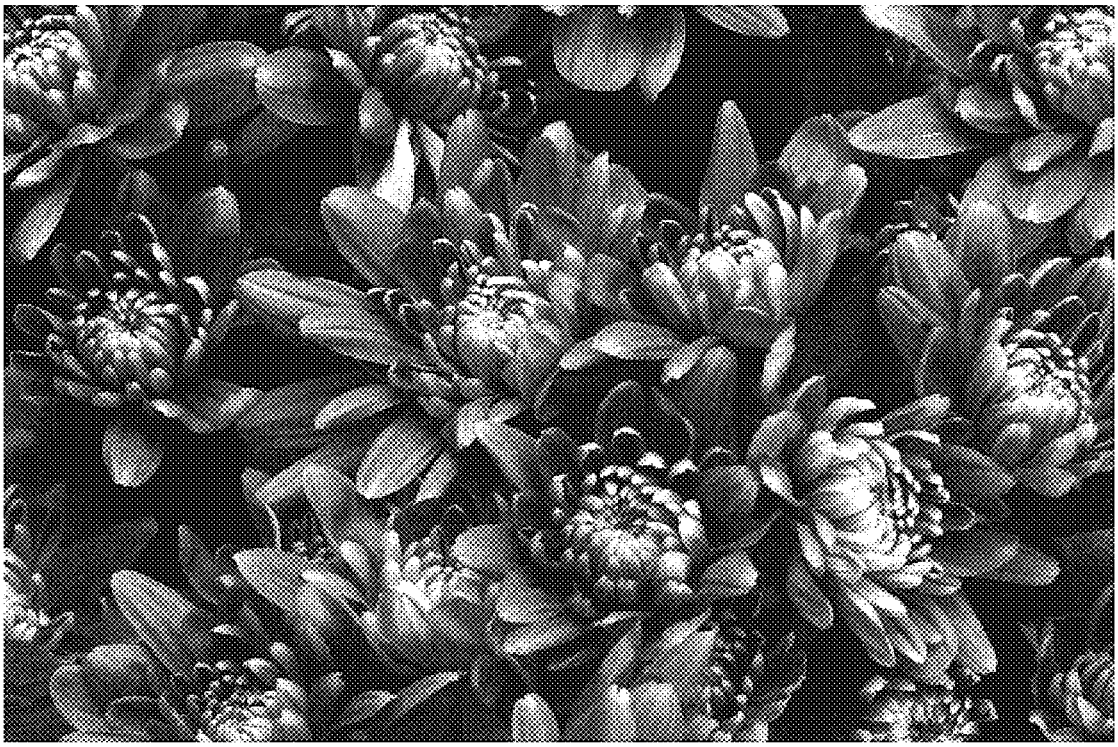

* * * * *